(12) United States Patent
Tanaami

(10) Patent No.: US 7,125,710 B2
(45) Date of Patent: Oct. 24, 2006

(54) APPARATUS FOR MEASURING THE GENETIC SEQUENCE OF BIOPOLYMERS

(75) Inventor: Takeo Tanaami, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 555 days.

(21) Appl. No.: 09/927,049

(22) Filed: Aug. 9, 2001

(65) Prior Publication Data
US 2002/0028502 A1 Mar. 7, 2002

(30) Foreign Application Priority Data
Sep. 7, 2000 (JP) .............................. 2000-271357

(51) Int. Cl.
C12M 1/34 (2006.01)
C12Q 1/68 (2006.01)
G01N 27/403 (2006.01)

(52) U.S. Cl. .................... 435/287.2; 435/6; 435/288.7; 204/600; 204/643

(58) Field of Classification Search .................... 435/6, 435/285.2, 287.2; 204/600, 403.1, 403.2, 204/403.3
See application file for complete search history.

(56) References Cited

U.S. PATENT DOCUMENTS 5,605,662 A * 2/1997 Heller et al. ................ 422/68.1
5,632,957 A 5/1997 Heller et al.
6,051,380 A 4/2000 Nerenberg et al.
6,238,909 B1 * 5/2001 Choong et al. ........... 435/287.2
2001/0005718 A1 * 6/2001 Wen-Tung et al. ........... 514/44

FOREIGN PATENT DOCUMENTS

EP 1120646 8/2001
WO WO 9739144 A1 * 10/1997
WO 013848-2 5/2001

OTHER PUBLICATIONS

RG Sosnowski et al "Rapid Determination of single base mismatch mutation in DNA hybrids by direct electric field control" Feb. 97, Proc. Natl Acad Sci USA vol. 94, pp. 1119-1123.

* cited by examiner

Primary Examiner—William H. Beisner
(74) Attorney, Agent, or Firm—Moonray Kojima

(57) ABSTRACT

The present invention relates to apparatus for measuring the genetic sequence of electrically charged biopolymers by means of hybridization. The measuring apparatus comprises a container that contains a biopolymer and can be removed from the apparatus, and electrodes that apply an electric field to the container and are electrically insulated from the container. When an electric field is applied to the container, suspended biopolymeric molecules are attracted toward the positive electrode, thus increasing the speed of hybridization.

6 Claims, 4 Drawing Sheets

APPARATUS FOR MEASURING THE GENETIC SEQUENCE OF BIOPOLYMERS

BACKGROUND OF THE INVENTION

1. Field of the Invention

The present invention relates to apparatus for measuring the genetic sequence of biopolymers, such as DNA and protein.

2. Description of the Prior Art

The DNA chip for hybridization described in the published Japanese translation of patent application Ser. No. 512,605 of 1999 is configured in such a manner that a large number of electrodes are formed on a substrate and a current source is connected to each of these electrodes. There are 100 to 10,000 electrodes on the substrate and, in normal applications, a different type of DNA segment is fixed to each electrode.

By flowing unknown DNA segments onto the substrate to which known DNA segments are fixed for hybridization as described above, it is possible to have an unknown DNA segment combine with its corresponding DNA segment. If the unknown DNA segment is labeled with a fluorescent reagent, the sequence of the unknown DNA segment that has combined with any known DNA segment can be determined.

The prior art cited above will now be described in further detail. As shown in FIG. 1, a positive voltage is applied to an electrode 1 to which a known DNA segment indicated by 2 is fixed. Since DNA is negatively charged, an unknown DNA segment indicated by 3 is attracted toward the electrode 1 where the known DNA segment 2 is fixed, as shown in FIG. 1b. As a result, hybridization that used to take several hours to finish is completed in only several tens of seconds.

The combining force is weak in case known and unknown DNA segments with different sequences wrongly combine with each other, as shown in FIG. 2a. Thus means the segment pair can be separated by applying a weak negative voltage to the electrode 1 after hybridization, as shown in FIG. 2b. Thus, it is possible to precisely measure even a single-base difference as seen in such DNA samples as SNPs (single nucleotide polymorphisms).

Such a DNA chip as described above is housed in a cartridge together with, for example, a fluid system combined with a detection system.

This DNA chip has had the following problems, however:

1) Cartridges are designed to be disposable, as a rule. On the other hand, the prior art cartridge requires a large number of electrodes and electrical connection terminals to be formed thereon and, therefore, is costly. Furthermore, electrodes and their processing circuits are also required for a reading unit used with the cartridge. Thus, the cost of a total system also is high.

2) Since the electrical connections of the DNA chip are made of electrodes, metal surfaces in contact with a solution are liable to cause electrochemical noise or fluctuations. Furthermore, electrical contact with the terminals of the reading unit tends to become defective.

3) The DNA chip requires electrodes and their electrical taps to be formed on the cartridge, thereby increasing the size of the cartridge. The reading unit also requires such elements as terminals and voltage supply circuitry.

SUMMARY OF THE INVENTION

An object of the present invention is to solve the above-mentioned problems, by providing inexpensive and highly reliable apparatus that uses small containers and measures the genetic sequence of biopolymers.

In order to attain the above-described object, according to claim 1 of the present invention, an apparatus is provided for measuring the genetic sequence of electrically charged biopolymers by means of hybridization, wherein the measuring apparatus comprises a container that contains a biopolymer and can be removed from the apparatus and electrodes that apply electric fields to the container and are electrically insulated therefrom.

This measuring apparatus configuration provides the following advantageous effects:

When electric fields are applied to the container, suspended biopolymeric molecules are attracted toward the positive electrode, thereby increasing the speed of hybridization. The container requires neither electrodes nor electrical connection terminals and is therefore inexpensive. Furthermore, a reading unit used with the container requires no more than one pair of an electrode structure and processing circuitry. Thus, the system as a whole is also inexpensive. Since the container has no electrode structure, electrochemical noise or fluctuations are very unlikely and, therefore, failures due to defective electrical contact with the terminals of the reading unit will never occur. The measuring apparatus requires neither electrodes nor their electrical taps to be formed on the container, thereby reducing the size of the container. The reading unit can also be downsized since the unit requires no more than one pair of an electrode structure and voltage source circuitry.

According to a feature of the present invention, the above-mentioned measuring apparatus may be provided with means for altering the direction of an electric field applied through electrodes, so that wrongly hybridized segment pairs are easily separated.

According to another feature of the present invention, the container may be formed using a film. If the container is made of a film, sites and electrodes can be easily brought close to each other, thus, the electric field can be positioned with higher precision and the cost of the container can be reduced.

According to a further feature of the present invention, the electrodes may be provided with protrusions formed at spatial positions corresponding to sites where biopolymeric molecules within the container gather. This configuration is advantageous since electric field strength can be made intensive at specific locations.

According to another feature of the present invention, conductive members may be formed at positions corresponding to sites where biopolymeric molecules within the container gather.

According to a further feature of the present invention, the electrodes may be placed in mechanical contact with the container.

According to another feature of the present invention, the electrodes may be of transparent type.

According to a further feature of the present invention, the transparent electrodes may be formed using an ITO film.

According to another feature of the present invention, the biopolymer may be either DNA, RNA, PNA or electrically charged protein.

DETAILED DESCRIPTION OF THE PREFERRED EMBODIMENTS

Figure 1A:
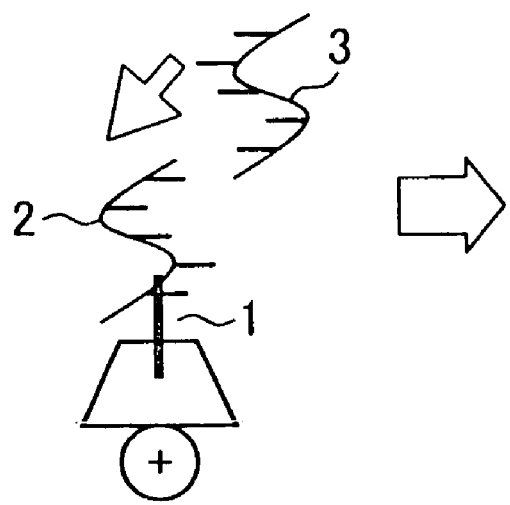
FIG. 1 is a schematic view explaining how DNA segments are attracted toward an electrode.
Figure 1B:
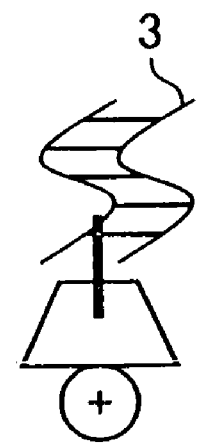
Figure 2A:
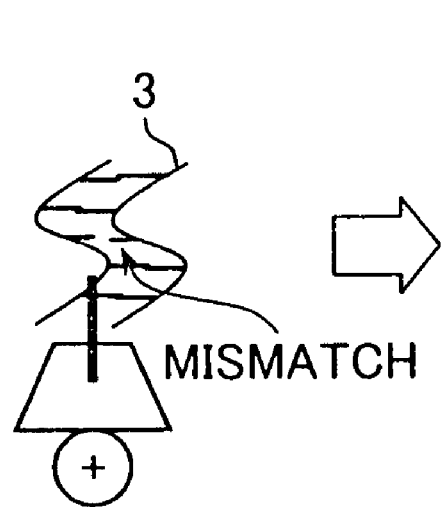
FIG. 2 is a schematic view explaining how combined DNA segments are separated once again.
Figure 2B:
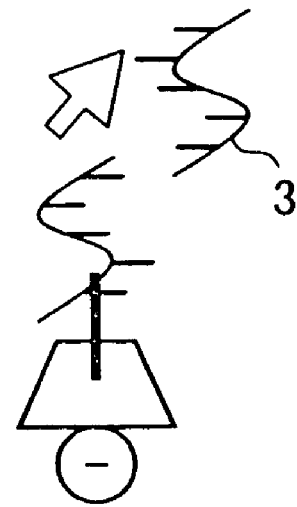
Figure 3A:
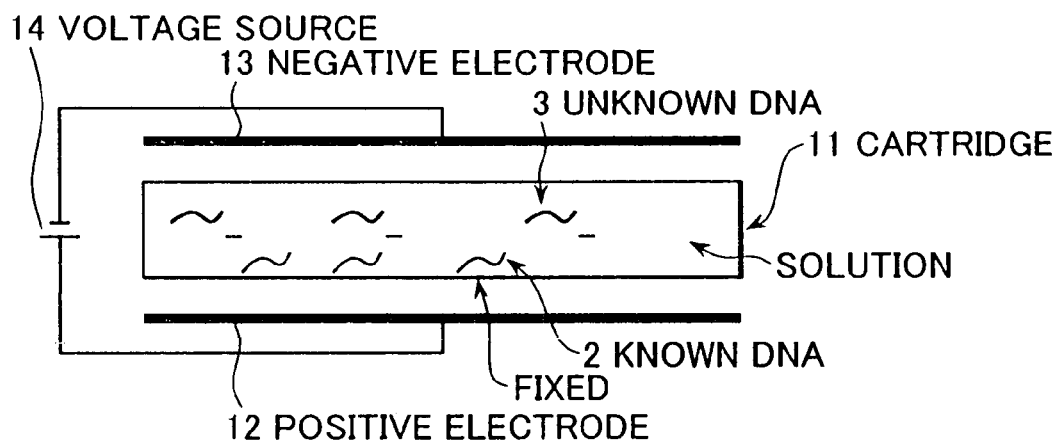
FIG. 3 is a schematic view showing one embodiment of the measuring apparatus according to the present invention.

Preferred embodiments will now be described in detail with reference to the accompanying drawings. FIG. 3 is a schematic view showing one embodiment of the measuring apparatus according to the present invention. In FIG. 3a, a numeral 11 indicates a container which is made of an insulator and into which a solution containing DNA is injected (corresponds to a conventional cartridge and, therefore, may also be referred to as a cartridge), and numerals 12 and 13 denote positive and negative electrodes, respectively. The electrodes 12 and 13 are arranged so as to sandwich the container. Note that the cartridge 11 and the electrodes 12 and 13 are supported by means of known mechanisms. However, the mechanisms are excluded from the explanation of the embodiment.

A numeral 14 indicates a voltage source for generating voltage to be applied to the electrodes 12 and 13.

Hermetically sealed within the cartridge 11 is a solution containing known and unknown DNA segments, wherein the known DNA segments are fixed onto the inner wall (bottom side in the figure) of the cartridge 11.

Figure 3B:
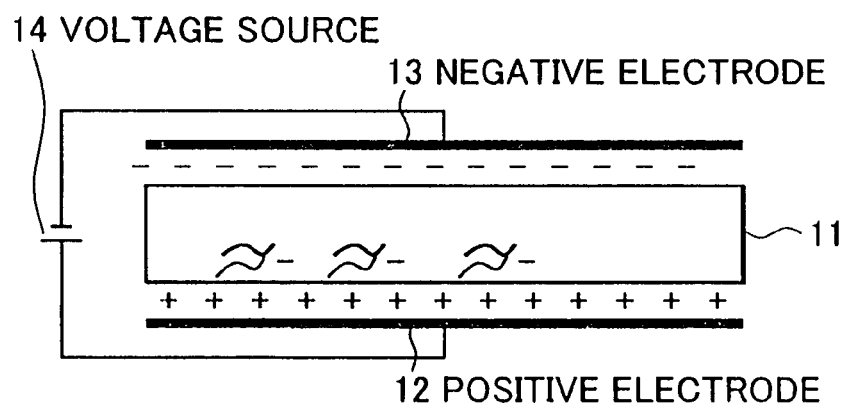

When a voltage is supplied by the voltage source 14 to the electrodes 12 and 13, an unknown DNA in suspension is attracted toward the positive electrode 12, as shown in FIG. 3b, since the unknown DNA segment is negatively charged. Thus, the unknown DNA segment approaches toward a known DNA segment. As a result, the speed of hybridization is increased.

By reversing the electrode polarity after hybridization, it is possible to separate wrongly hybridized DNA segment pairs. Consequently, it is possible to precisely measure even a one-base difference as seen in SNPs.

Figure 4:
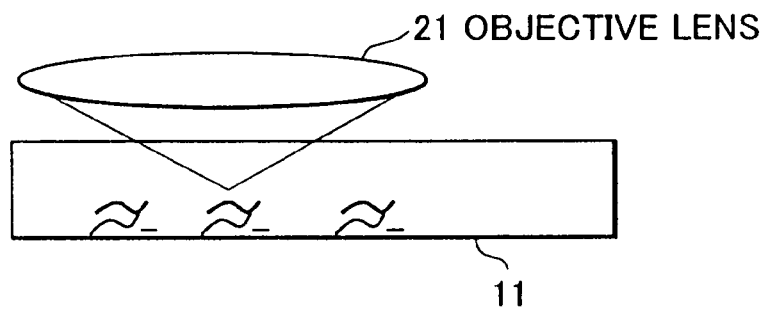
FIG. 4 is a schematic view explaining how DNA segments are observed through an objective lens.

It is possible to label DNA segments with a fluorescent reagent and observe the segments in the same way as practiced in the prior art. Preferably, the electrodes 12 and 13 are configured so that the electrodes can be removed from the cartridge 11 after hybridization. Removing the electrodes 12 and 13 from the cartridge 11 after hybridization will make it easy to observe the cartridge 11 through an objective lens 21, as shown in FIG. 4.

It should be noted that the present invention is by no means limited to the above-described embodiment. The invention may be embodied in other ways without departing from the spirit and essential characteristics thereof. Accordingly, it should be understood that all modifications falling within the spirit and scope of the present invention are covered by the appended claims.

Figure 5:
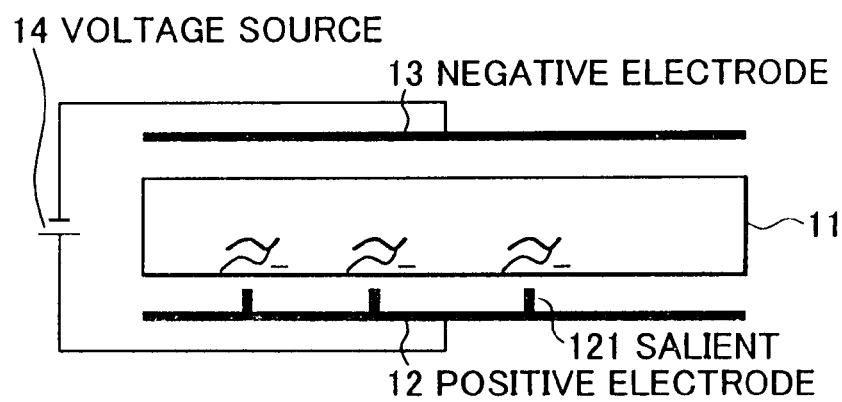
FIG. 5 is a schematic view showing another embodiment of the measuring apparatus according to the present invention.

For example, the positive electrode 12 may be alternatively configured in such a manner that a protrusion 121 extending toward the cartridge 11 is formed on the electrode at a position corresponding to each site (also referred to as a "spot") of DNA, as shown in FIG. 5. By employing this electrode configuration, it is possible to make electric field strength intensive at the site.

Figure 6:
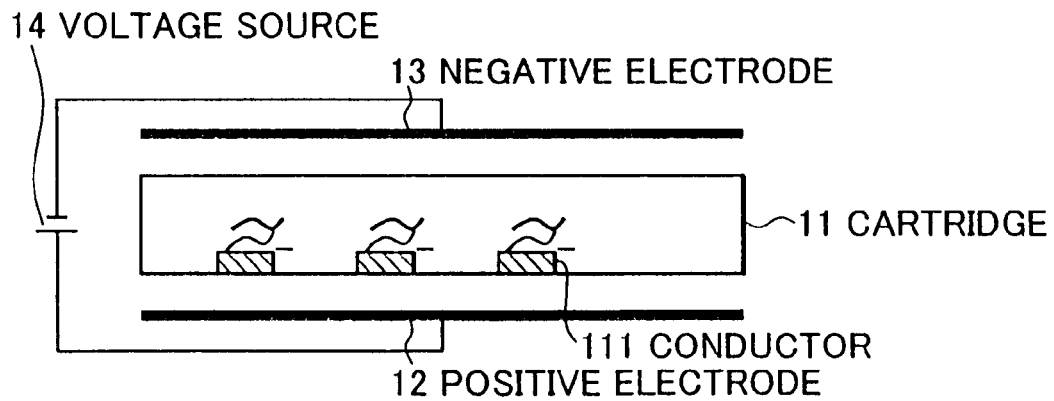
FIG. 6 is a schematic view showing yet another embodiment of the measuring apparatus according to the present invention.

Alternatively, a conductive member (conductor) 111 may be formed at the position of each site on the inner wall of the cartridge 11, as shown in FIG. 6. In this case, a known DNA segment is previously fixed onto the topside of the conductor 111.

Alternatively, the present invention may be carried out by combining the embodiments of FIGS. 5 and 6.

Alternatively, the electrodes 12 and 13 may be placed in contact with the cartridge 11 if the cartridge 11 is formed using plastic or any other insulator. This configuration is possible since the only requirement in this case is that the electrodes 12 and 13 be electrically isolated from the cartridge 11. Mechanical contact is advantageous in stabilizing the positional relationship between the electrodes and the cartridge.

Figure 7:
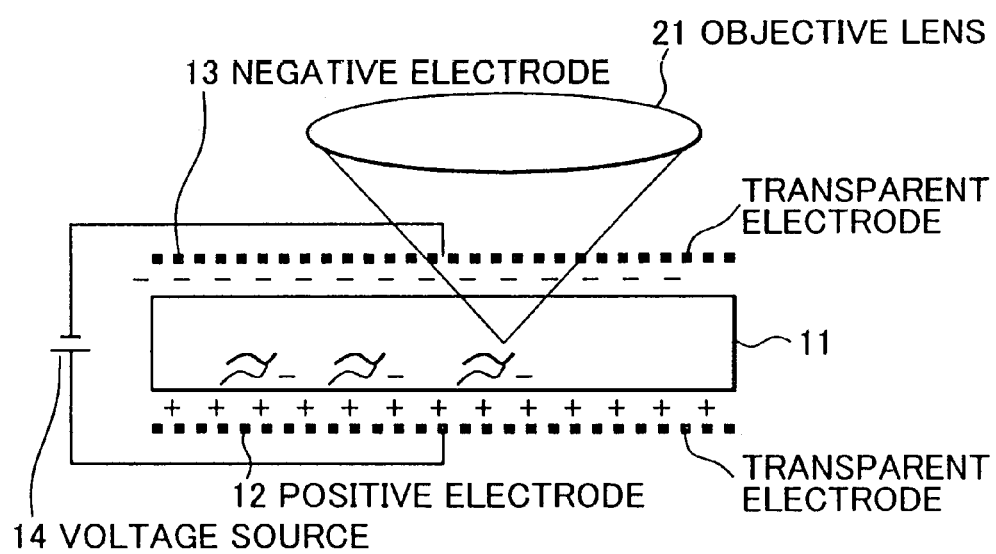
FIG. 7 is a schematic view showing yet another embodiment of the measuring apparatus according to the present invention.

Alternatively, transparent electrodes like those made of an ITO (Indium Tin Oxide) film may be used as the electrodes 12 and 13, as shown in FIG. 7. Use of transparent electrodes is advantageous since fluorescence observation is still practicable without having to move the electrodes.

Note that fluorescence may be measured with the internal solution drained out of the cartridge 11 and the cartridge dried out.

Alternatively, the cartridge 11 may be made of a thin film. This configuration reduces the distance between sites and the electrode. Consequently, the configuration is advantageous in the case of the embodiments of FIGS. 5 and 6 since the positional accuracy of an electric field can be improved.

Although the case where sites are made of DNA has been explained, the present invention is not limited to this case. Alternatively, the sites may be made of RNA, PNA (peptide nucleic acid), or electrically charged protein.

As described heretofore, the present invention has the following advantageous effects:

1) There is no need for forming electrodes and electrical connection terminals on a cartridge, thus reducing the cost thereof. Furthermore, a reading unit used with the cartridge requires no more than one pair of an electrode structure and processing circuitry. Thus, the system as a whole is also inexpensive.

2) Since the container has no electrode structure, electrochemical noise or fluctuations are very unlikely. Furthermore, electrical contact with the terminals of the reading unit never becomes defective.

3) There is no need for forming electrodes and their electrical taps on the container, thereby reducing the size of the container. The reading unit can also be downsized since the unit requires no more than one pair of an electrode structure and voltage source circuitry.

What is claimed is:

1. A measuring apparatus for measuring genetic sequence of electrically charged biopolymers by hybridization, said apparatus comprising:
    a container that contains known biopolymer segments fixed onto an inner wall of said container and unknown biopolymer segments existing in a solution contained within said container, which are to be hybridized, said container being removable from said measuring apparatus; and one or more electrodes disposed to be adjacent to said container for applying an electric field to said container, said one or more electrodes being electrically insulated from said container, and further being provided with protrusions formed at spatial positions corresponding to sites of the known biopolymer segments fixed within said container, wherein conductive members are formed in the container at spatial positions corresponding to said sites.

2. The apparatus of claim 1, wherein said biopolymer segments are DNA,RNA,PNA or electrically charged proteins.

3. The apparatus of claim 1, wherein said container is made of a film.

4. A measuring apparatus for measuring genetic sequence of electrically charged biopolymers by hybridization, said apparatus comprising:

a container that contains known biopolymer segments fixed onto an inner wall of said container and unknown biopoymer segments existing in a solution contained within said container which are to be hybridized, said container being removable from said measuring apparatus;

one or more electrodes disposed to be adjacent to said container for applying an electrical field to said container, said one or more electrodes being electrically insulated from said container; and means for altering direction of said electrical field so that wrongly hybridized segment pairs are separated; wherein said one or more electrodes are provided with protrusions formed at spatial positions corresponding to sites of the known biopolymer segments fixed within said container; wherein conductive members are formed in the container at spatial positions corresponding to said sites.

5. The apparatus of claim 4, wherein said biopolymer segments are DNA,RNA,PNA or electrically charged proteins.

6. The apparatus of claim 4, wherein said container is made of a film.

* * * * *